(12) United States Patent
Narimatsu

(10) Patent No.: US 7,029,442 B2
(45) Date of Patent: Apr. 18, 2006

(54) VITAL-INFORMATION MEASURING DEVICE

(75) Inventor: Kiyoyuki Narimatsu, Komaki (JP)

(73) Assignee: Colin Medical Technology Corporation, Komaki (JP)

(*) Notice: Subject to any disclaimer, the term of this patent is extended or adjusted under 35 U.S.C. 154(b) by 70 days.

(21) Appl. No.: 10/825,374

(22) Filed: Apr. 16, 2004

(65) Prior Publication Data

US 2004/0260184 A1 Dec. 23, 2004

(30) Foreign Application Priority Data

Apr. 21, 2003 (JP) .............................. 2003-116291

(51) Int. Cl.
*A61B 5/00* (2006.01)
(52) U.S. Cl. ...................... 600/300; 128/920
(58) Field of Classification Search .................. None
See application file for complete search history.

(56) References Cited

U.S. PATENT DOCUMENTS 3,977,394 A * 8/1976 Jones et al. ................. 600/541
4,463,764 A * 8/1984 Anderson et al. ........... 600/532

FOREIGN PATENT DOCUMENTS

| JP | U 58-179102 | 11/1983 |
|---|---|---|
| JP | A 62-170228 | 7/1987 |
| JP | A 06-142065 | 5/1994 |
| JP | A 07-236617 | 9/1995 |
| JP | A 7-284480 | 10/1995 |
| JP | U 3024751 | 3/1996 |
| JP | A 11-178802 | 7/1999 |
| JP | A 2003-024287 | 1/2003 |

* cited by examiner

*Primary Examiner*—Max F. Hindenburg
*Assistant Examiner*—Patricia C. Mallari
(74) *Attorney, Agent, or Firm*—Oliff & Berridge, PLC

(57) ABSTRACT

The measurement results judging means 80 judges whether or not the measurement of vital signal. In the case where it has been judged that all of the measurements of the vital signal used for the measurement of such plurality of vital-information are normal, since the above-described plurality of vital-information are automatically output from the printer 58, the troublesome works of the printing operation can be omitted, and in the case where it has been judged that the measurement of the vital signals used for the determination of at least one of the vital-information is not normal, the above-described vital-information is not output from the printer 58, therefore, unnecessary vital-information can be prevented from being output from the printer 58.

2 Claims, 7 Drawing Sheets

VITAL-INFORMATION MEASURING DEVICE

This application is based on Japanese Patent Application No.2003-116291 filed Apr. 21, 2003, the contents of which are incorporated hereinto reference.

BACKGROUND OF THE INVENTION

1. Field of the Invention

The present invention relates to a vital-information measuring device for measuring biological information.

2. Prior Art

In the case where a patient is diagnosed, a variety of vital signals are detected from the patient and vital-information are measured based on the vital signals. For example, in the case where the blood pressure is measured as a vital-information, pulse waves, Korotkoff sounds or the others are detected as a vital signal.

Since the measured vital-information is necessary to be recorded, there are many cases in which a vital-information measuring device is equipped with a printer, and the measured vital-information is printed out from the printer (for example, see Patent Document 1). In the Patent Document 1, the measured vital-information is automatically printed out from the printer. In this way, if it is made such that the vital-information is automatically printed out from the printer, the troublesome works for operating the printing from the printer each time when the printing out is needed can be omitted, and also the printing can be prevented from being forgot. Patent Document 1

Japanese Unexamined Patent Publication No.H07-284480 gazette

As described in the Patent Document 1, in the case where the determined vital-information is automatically printed out, even in the case where the measurement of the vital signals for the purpose of determining the vital-information cannot be normally carried out due to a body movement and the like of the patient, as a result, it may be inconvenient such that the vital-information is printed out even if the vital-information determined based on the vital signals does not have the reliability.

The present invention has been made on the background of the above-described circumstances, and an object of the present invention is to provide a vital-information measuring device in which the troublesome works for operating the printing can be omitted as much as possible and unnecessary vital-information is not printed out from the printer.

SUMMARY OF THE INVENTION

The above object may be achieved according to the present invention, which provides a vital-information measuring device, comprising, (1) a vital signal sensor for detecting a vital signal, (2) a vital-information determining means for determining a vital-information based on the vital-information detected by the vital signal sensor, and (3) a printer for outputting vital-information determined by the vital-information determining means, (4) a measurement results judging means for judging whether or not the vital signal measured by the vital signal sensor is a signal normally measured based on a predetermined judging criterion, and (5) output control means for control the printer such that the printer does not print out the vital-information when the measurement of said vital signal was judged as not being normal by the judging means, and the printer print out the vital-information when the measurement of the vital signal was judged as being normal by the judging means.

According to the first aspect of the present invention, whether or not the measurement of the vital signals for judging the vital-information is normal is automatically determined by the measurement results judging means, in case where it is judged that the measurement of the vital signals is normal, the vital-information is automatically printed out from the printer, therefore, the troublesome works for operating the printing is omitted, and in the case where it has been judged that the measurement of the vital-information is not normal, the vital-information is not printed out from the printer, therefore, the unnecessary vital-information can be prevented from being printed out from the printer.

In the first preferred form of the present invention, the 2. The vital-information measuring device further comprises: (1) a display for indicating the vital signal used for determination of said vital-information and a characteristic value of the vital signal; (2) a message indicating means for indicating on the display a message requesting the judgment on whether or not the vital-information is output from said printer when the measurement of said vital signal was judged as not being normal by the measurement results judging means; and (3) an output command button for being operated by an operator in order to print out said vital-information from said printer, (4) wherein when the output command button is operated, even if the measurement of said vital signal has been judged as not being normal by the measurement results judging, said output control means controls the printer so as to output said vital-information.

Even in the case where it has been judged by the measurement results judging means that the measurement of the vital signals is not normal, there are some cases in which the abnormality of the measured vital signals is based on a disease of the patient and it is not the error of the measurement itself. However, according to the first preferred form of the present invention if it is done in that way, in the case where it has been judged by the measurement results judging means that the measurement of the vital signals is not normal, since the vital signals or their values of characteristics used for the determination of the vital-information are indicated on a display by message displaying means, a physician and the other co-medicals can determine whether or not the measurement of the vital signals is normal, even in the case where it has been judged by the means for judging the measurement results that the measurement of the vital signals is not normal, when the operator operates the output command button, the vital-information is printed out from the printer. Therefore, necessary vital-information can be certainly printed out from the printer.

Moreover, the vital-information determining means may determine only one species of vital-information, however, a plurality of species of vital-information may be also determined. In the case where a plurality of species of vital-information are determined in that way, the second preferred form of the vital-information measuring device according to the present invention is preferably used, wherein (1) the vital-information determining means determines a plurality of species of vital-information, (2) the measurement results judging means judges the each vital-information of the plurality of species whether or not a vital signal used for judgment of the vital-information is a signal normally measured, (3) the output control means controls the printer so as to automatically output the vital-information determined by the vital-information determining means when the measurement of a vital signal used for determination of all the vital-information was judged as being normal by the measurement results judging means, however, the output control means does not control the printer to output the plurality of vital-information determined by vital-information determining means when measurement of the vital signal used for determination of at least one of said vital-information was judged as not being normal. If it is done in this way, even in the case where a plurality of species of vital-information is determined, unnecessary vital-information can be prevented from being printed from the printer.

Moreover, in this way, at the time when it has been judged that the measurement of the vital signals used for the determination of at least one vital-information is not normal, even in the case where it is made so that these multiple vital-information is not printed out from the printer, it is preferable that a physician or the other co-medical finally judges whether or not it is necessary to print out these multiple vital-information from the printer. Therefore, in a third preferred form of the vital-information measuring device according to the present invention, the vital-information measuring device further comprises: (1) a display for indicating a vital signal used for determination of said plurality of vital-information or a characteristic value of the vital signal; (2) a message indicating means for indicating a message requesting the judgment on whether or not said plurality of vital-information is output from said printer on the display when measurement of vital signals used for determination of at least one of said vital-information was judged as not being normal by the measurement results judging means and; (3) an output command button operated by an operator in order to print out said vital-information from said printer, (4) wherein said output control means controls the printer so as to automatically output the plurality of vital-information when the output command button was operated even if the measurement of said vital signal used for determination of at least one of said vital-information by the measurement results judging means was judged as not being normal.

BRIEF DESCRIPTION OF THE DRAWINGS

The above and other objects features, advantages and technical and industrial significance of the present invention will be better understood by reading the following detailed description of presently preferred embodiment of the invention, when considered in connection with the accompanying drawings, in which:

FIG. 5 is a diagram for indicating a control function of an electronic control device shown in. FIG. 2 as a flowchart and is an ankle and upper arm blood pressure index ABI calculation routine;

DETAILED DESCRIPTION OF PREFERRED EMBODIMENTS

Figure 1:
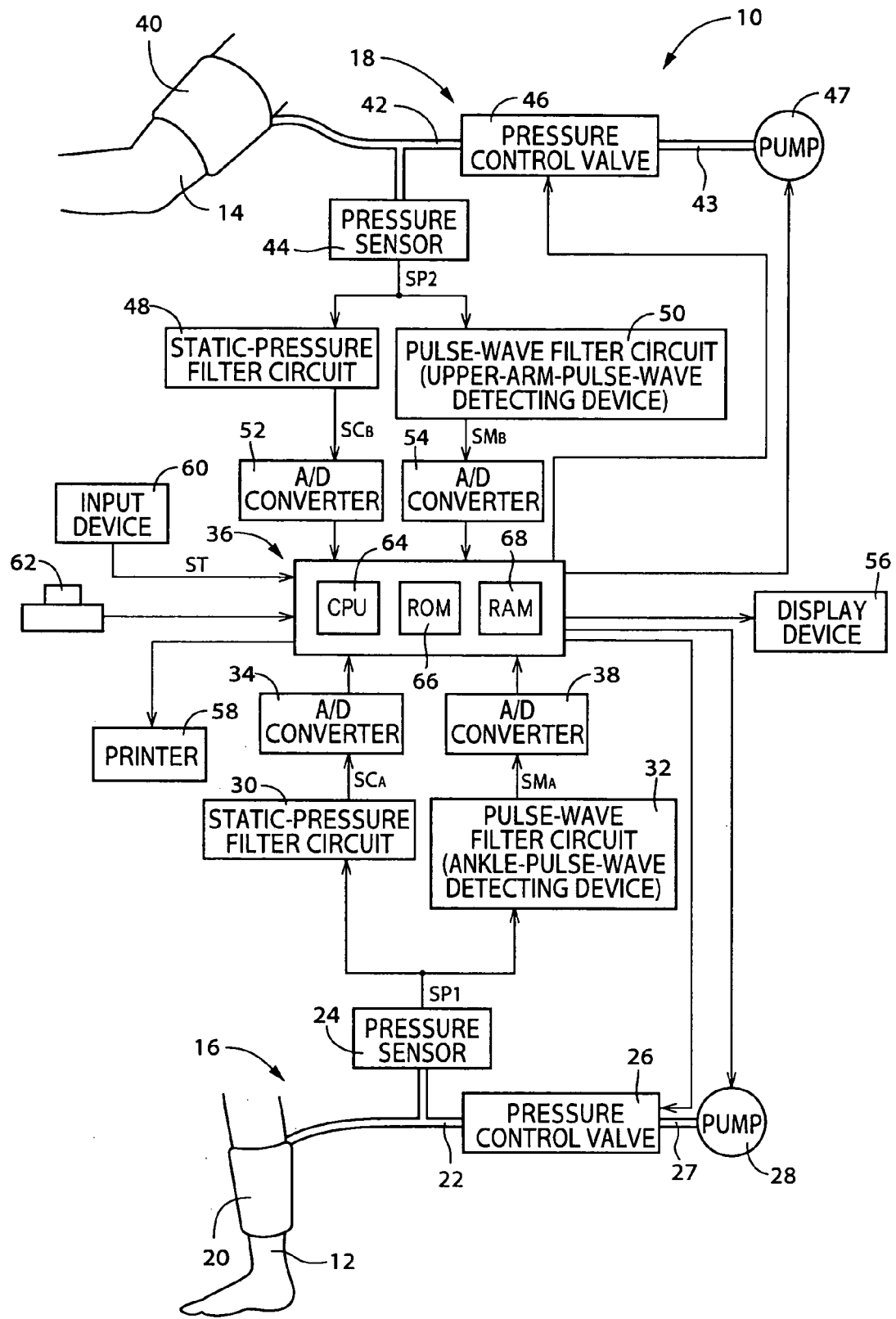
FIG. 1 is a block diagram for illustrating an arteriosclerosis diagnosing device functioning as a vital-information measuring device of the present invention.

Hereinafter, there will be described one embodiment of the present invention, by reference to the drawings. FIG. 1 is a diagrammatic view foe explaining the construction of an arteriosclerosis evaluating apparatus 10 to which the present invention is applied. The arteriosclerosis evaluating apparatus 10 determines vital information such as a pulse wave velocity PWV, an upper arm blood-pressure BP(B), an ankle blood-pressure BP(A), and an inferior-and-superior-limb blood-pressure-index ABI, for evaluating an arteriosclerosis of a living subject.

As shown in FIG. 1, the arteriosclerosis evaluating apparatus 10 includes an ankle BP measuring device 16 which measures a BP value of the ankle 12 (e.g., a right ankle) and which functions as an inferior-limb BP measuring device, and an upper-arm BP measuring device 18 which measures a BP value of the upper arm 14 and functions as a superior-limb BP measuring device.

The ankle BP measuring device 16 includes an ankle cuff 20 which includes a belt-like cloth bag and a rubber bag accommodated in the cloth bag and which is adapted to be wound around the ankle 12 of the patient; a piping 22; and a pressure sensor 24, a pressure control valve 26, and an air pump 28 which are connected to the ankle cuff 20 via the piping 22. The pressure control valve 26 adjusts a pressure of a pressurized air supplied from the air pump 28, and supplies the pressure-adjusted air to the ankle cuff 20, or discharges the pressurized air from the ankle cuff 22, so as to control an air pressure in the ankle cuff 20.

The pressure sensor 24 detects the air pressure in the ankle cuff 20, and supplies a pressure signal, SP1, representing the detected air pressure, to a static-pressure filter circuit 30 and a pulse-wave filter circuit 32. The static-pressure filter circuit 30 includes a low-pass filter which extracts, from the pressure signal SP1, an ankle-cuff-pressure signal, $SC_A$, representing a static component of the detected air pressure, i.e., a pressing pressure of the ankle cuff 20 (hereinafter, referred to as the ankle-cuff pressure, $PC_A$). The filter circuit 30 supplies the ankle-cuff-pressure signal $SC_A$ to an electronic control device 36 via an A/D (analog-to-digital) converter 34.

The pulse-wave filter circuit 32 includes a band-pass filter which extracts, from the pressure signal SP1, an ankle-pulse-wave signal $SM_A$, representing an ankle pulse wave as an oscillatory component of the detected air pressure that has prescribed frequencies. The filter circuit 32 supplies the ankle-pulse-wave signal $SM_A$ to the control device 36 via an A/D converter 38. Since the ankle pulse wave indicates the oscillation of pressure of the ankle cuff 20, the filter circuit 32 functions as an ankle-pulse-wave detecting device or an inferior-limb-pulse-wave detecting device.

The upper-arm BP measuring device 18 includes an upper-arm cuff 40 having a construction identical with that of the cuff of the ankle BP measuring device 16; and a piping 42, a pressure sensor 44, a pressure control valve 46, static-pressure filter circuit 48, and a pulse-wave filter circuit 50. The upper-arm cuff 40 is wound around the upper arm 14. The pressure control valve 46 is connected to the air pump 28.

The pressure sensor 44 detects an air pressure in the upper-arm cuff 40, and supplies a pressure signal, SP2, representing the detected air pressure, to a static-pressure filter circuit 48 and a pulse-wave filter circuit 50 which have respective constructions identical with those of the counterparts of the ankle BP measuring device 16. The static-pressure filter circuit 48 extracts, from the pressure signal SP2, an upper-arm-cuff-pressure signal, $SC_B$, representing a static component of the detected air pressure, i.e., a pressing pressure of the upper-arm cuff 40 (hereinafter, referred to as the upper-arm-cuff pressure, $PC_B$). The filter circuit 48 supplies the upper-arm-cuff-pressure signal $SC_B$ to the control device 36 via an A/D converter 52. The pulse-wave filter circuit 50 extracts, from the pressure signal SP2, an upper-arm-pulse-wave signal, $SM_B$, representing an upper-arm pulse wave as an oscillatory component of the detected air pressure that has prescribed frequencies. The filter circuit 50 supplies the upper-arm-pulse-wave signal $SM_B$ to the control device 36 via an A/D converter 54. Since the upper-arm pulse wave indicates the oscillation of pressure of the upper-arm cuff 40, the filter circuit 50 functions as an upper-arm-pulse-wave detecting device or a superior-limb-pulse-wave detecting device.

Display device 56 displays an ankle-pulse-wave signal $SM_A$ and an upper-arm-pulse-wave signal $SM_B$ and also displays an arm blood-pressure BP(B), an ankle blood-pressure BP(A), and ABI value measured by the control device 36. Printer 58 prints the determined pulse wave velocity PWV, upper arm blood-pressure BP(B), ankle blood-pressure BP(A), and ABI value.

An input device 60 is equipped with a plurality of numeric input keys which are not shown in the figures for inputting a body height T of a patient, and supplying a body height signal ST indicating the input body height of the patient into an electronic control device 36. An output command button 62 is a button for operating it for the purpose of outputting the above-described pulse wave velocity (PWV), upper arm blood pressure BP(B), ankle blood pressure BP(A) and ankle and upper arm blood pressure index ABI and the like, at the time when the output command button 62 is operated, an output command signal is supplied to an electronic control device 36.

The control device 36 is essentially provided by a microcomputer including a CPU (central processing unit) 64, a ROM (read only memory) 66, a RAM (random access memory). 68, and an I/O (input-and-output) port, not shown, and the CPU 56 processes signals according to the programs pre-stored in the ROM 66, while utilizing the data-storing function of the RAM 68. The control device 36 outputs, from the I/O port, drive signals to the air pump 28 and the two pressure control valves 26, 46 so as to control the respective operations thereof and thereby control the respective air pressures of the ankle cuff 20 and the upper-arm cuff 40. In addition, the CPU 56 processes signals supplied to the control device 36, so as to determine an ankle-and-upper-arm BP index (hereinafter, referred to as an ABI value) and control a display device 56 and printer 58 to display and print the determined pulse wave velocity PWV, upper arm blood-pressure BP(B), ankle blood-pressure BP(A), and ABI value.

Figure 2:
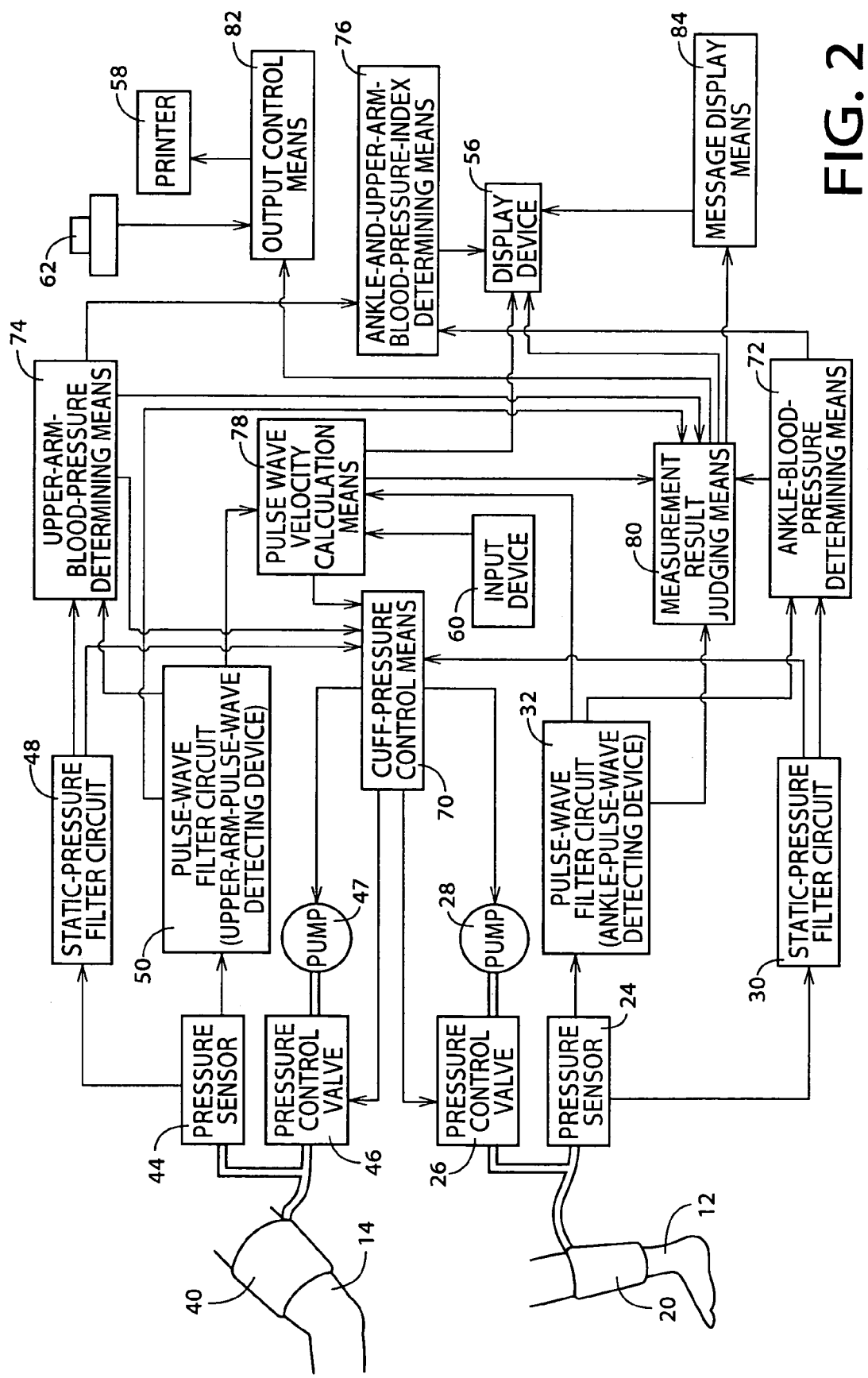
FIG. 2 is a functional block diagram for indicating the major portion of a control function of an electronic control device in an arteriosclerosis diagnosing device of FIG. 1.

FIG. 2 is a functional block diagram indicating the major portion of control function of the electronic control device 36. Cuff pressure control means 70 controls two air pumps 28, 47 and two pressure regulating valves 26, 46 connected to the two air pumps 28,47, respectively, while determining ankle cuff pressure $PC_A$ and upper arm cuff pressure $PC_B$ based on ankle cuff pressure signal $SC_A$ and upper arm cuff pressure signal $SC_B$ supplied from static pressure discrimination circuits 30, 48 according to the command signal from ankle blood pressure value determination means 72 and upper arm blood pressure value determination means 74 which are described later and the cuff pressure control means 70 controls ankle cuff pressure $PC_A$ and upper arm pressure $PC_B$ as the followings: The upper arm cuff pressure $PC_B$ is rapidly raised to the predetermined second target pressure value $PC_{M2}$ (for example, 180 mmHg) which is higher than the highest blood pressure value at the upper arm 14 as well as the ankle cuff pressure $PC_A$ is rapidly raised to the predetermined first target pressure value $PC_{M1}$ (for example, 240 mmHg) which is higher than the highest blood pressure value at the ankle 12, then, the ankle cuff pressure $PC_A$, and the upper arm cuff pressure $PC_B$ are gradually lowered on the order of 3–5 mmHg/sec. Furthermore, after the ankle lowest blood pressure value $BP(A)_{DIA}$ has been determined, the ankle cuff pressure $PC_A$ is made atmospheric pressure, and after the upper arm lowest blood pressure value $BP(B)_{DIA}$ has been determined, the upper arm cuff pressure $PC_B$ is made atmospheric pressure.

Moreover, the cuff pressure control means 70 controls the air pumps 28, 47 and the pressure regulating valves 26, 46 based on the command signal from the pulse wave velocity calculation means 78 which is described later, and controls the ankle cuff pressure $PC_A$ and the upper arm cuff pressure $PC_B$ into a predetermined pulse wave detection pressure, respectively. This pulse wave detection pressure is a pressure which is lower than the lowest blood pressure value at the site where cuffs 20, 40 are mounted, respectively, and is a pressure such that pulse wave signals $SM_A$, $SM_B$ which are discriminated by the pulse wave discrimination circuits 32, 50 become sufficient signal strength, for example, these are set at 50–60 mmHg.

Figure 3:
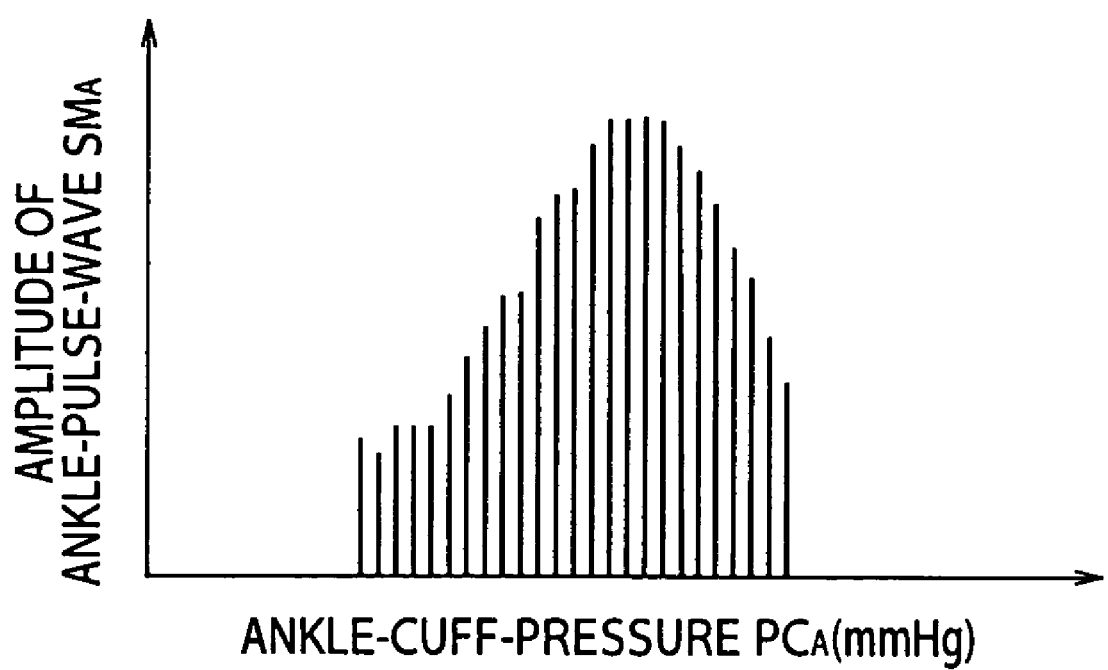
FIG. 3 is a drawing for exemplifying an amplitude row of an ankle pulse wave prepared upon the determination of an ankle blood pressure.

Ankle blood pressure value determining means 72 prepares an amplitude row constituted by the amplitude of the ankle pulse wave as shown in FIG. 3, from the amplitude of ankle pulse wave in turn detected in the process of gradually lowering the ankle cuff pressure $PC_A$ by the cuff pressure control means 70, smoothes the amplitude row by what is called a median process, and determines the ankle highest blood pressure value $BP(A)_{SYS}$, the ankle lowest blood pressure value $BP(A)_{DIA}$, the ankle mean blood pressure value $BP(A)_{MEAN}$ at the ankle 12 by the well known oscillometric algorithm based on the amplitude row after the smoothing. In the above-described oscillometric algorithm, for example, on the amplitude row after the smoothing, the ankle cuff pressure $PC_A$ at the rise up point of the envelope obtained by connecting the peak points of the respective amplitudes are considered to be ankle highest blood pressure value $BP(A)_{SYS}$, the ankle cuff pressure $PC_A$ at the peak point of the envelope is considered to be ankle mean blood pressure value $BP(A)_{MEAN}$, and the ankle cuff pressure $PC_A$ at the inflection point of differential curve that has differentiated the envelope (rise up point of the envelope) is considered to be ankle lowest blood pressure value $BP(A)_{DIA}$.

Upper arm pressure value determining Means 74 also functions as means for determining the vital-information, the means for determining the upper arm pressure value 74 determines the upper highest blood pressure value $BP(B)_{SYS}$, the upper lowest blood pressure value $BP(B)_{DIA}$, the upper arm mean blood pressure value $BP(B)_{MEAN}$ at the upper arm 14 based on the amplitude of the upper arm pulse wave in turn detected in the process of gradually lowering the upper arm cuff pressure $PC_B$ is by the cuff pressure control means 70 as similar to the means for determining the ankle blood pressure value 72.

Ankle and upper arm blood pressure indexes calculating means 76 also functions as means for determining the vital-information, the means for calculating the ankle and upper arm blood pressure indexes 76 calculates an ankle and upper arm blood pressure index ABI based on a value corresponding to the above-described ankle blood pressure value BP(A) at the ankle blood pressure value BP(A) determined by the means for determining the ankle blood pressure value 74 and at the upper arm pressure value BP(B) determined by the means for determining the upper arm blood pressure value 72, and displays the ankle and upper arm blood pressure index ABI calculated on a display 56. Here, the upper arm blood pressure value BP(B) corresponding to the ankle blood pressure value BP(A) refers to the highest blood pressure values and the like, respectively. Moreover, the ankle and upper arm blood pressure index ABI can be calculated by dividing the ankle blood pressure value BP(A) by the upper arm blood pressure value BP(B), or by dividing the upper arm blood pressure value BP(B) by the ankle blood pressure value BP(A).

Pulse wave velocity calculating means 78 also functions as means for determining the vital-information, the means for calculating the pulse wave velocity 78 reads out an ankle pulse wave signal $SM_A$ supplied from the pulse wave discrimination circuit 32 and an upper arm pulse wave signal $SM_B$ supplied from a pulse wave discrimination circuit 50, determines the predetermined site of the ankle pulse wave (peak, rise up point and the like) that the ankle pulse wave signal $SM_A$ represents and the site corresponding to the predetermined site of the above-described ankle pulse wave at the upper arm pulse wave that the upper arm pulse signal $SM_B$ represents, respectively, and calculates the time difference between the time when the predetermined site of the ankle pulse wave was detected and the time when the predetermined site of the upper arm pulse wave was detected. This time difference means a difference between the time required for propagation of the pulse wave from the heart to the ankle 12 and the pulse wave propagation time DT between the ankle 12 and the upper arm 14. Furthermore, the means for calculating the pulse wave velocity 78 finds the distance difference L between the propagation distance from the heart to the ankle 12 and the propagation distance from the heart to the upper arm 14 by substituting the body height T of the patient supplied from the input device 60 into the expression 1 which indicates the relationship previously memorized between the body height T and the distance difference L, and calculates the pulse wave velocity PWV (cm/sec) by substituting the obtained distance difference L and the above-described pulse wave propagation time DT.

$$L=aT+b \quad \text{(Expression 1)}$$

(where a, b are constants determined based on the experiment)

$$PWV=L/DT \quad \text{(Expression 2)}$$

It should be noted that the calculation of a plurality of pulse wave velocities PWVs might be performed only once, however, in order to enhance the reliability of the diagnosis, it is preferable that a plurality of pulse wave velocities PWVs are calculated and, therefore, in the present Example, the pulse wave velocity $PWV_{AV}$ is calculated based on the signal by the portion of 10 pulses, the average pulse wave velocity $PWV_{AV}$ that the pulse wave velocities PWVs by these 10 pulses were averaged is calculated and the average pulse wave velocity $PWV_{AV}$ is indicated on the display 56.

Measurement results judging means 80 judges whether or not the signal used for the determination of the ankle blood pressure value BP(A), the upper arm blood pressure value BP(B) and the pulse wave velocity PWV is a signal normally measured. Since the ankle blood pressure value BP(A) is determined based on the ankle pulse wave signal $SM_A$ supplied from the pulse wave discrimination circuit 32 in the process of gradually lowering pressure of the ankle cuff pressure $PC_A$, the upper arm blood pressure value BP(B) is determined based on the upper arm pulse wave signal $SM_B$ supplied from the pulse wave discrimination circuit 50 in the process of gradually lowering the upper arm cuff pressure $PC_B$, the pulse wave velocity PWV is determined from the ankle pulse wave signal $SM_A$ and the upper arm pulse wave signal $SM_B$ detected in the state where the ankle cuff pressure $PC_A$ and the upper arm cuff pressure $PC_B$ are controlled by the aforementioned pulse wave detection pressure, and the means for judging the measurement results 80 judges whether or not these signals were normally measured.

In order to determine whether or not the ankle pulse wave signal $SM_A$ used for the determination of the ankle blood pressure value BP(A) has been normally measured, for example, first, correction factor of the amplitude row of the pulse wave is calculated by the following method also described in Japanese Unexamined Patent Publication No.H07-236617 gazette and the like. Specifically, the percentage of the sum of the amplitude difference with respect to the amplitude values after the smoothing is calculated as a correction factor as well as the amplitude difference between the amplitude before the smoothing and the amplitude after the smoothing on each pulse wave based on the amplitude row before the smoothing and the amplitude row after the smoothing prepared by the means for determining the ankle blood pressure value 72. Then, in the case where the correction factor calculated is the predetermined reference value or less, it is judged that it has been normally measured. Moreover, it can be similarly judged whether or not the upper arm pulse wave signal $SM_B$ used for the determination of the upper arm blood pressure value BP(B) has been normally measured.

In order to determine whether or not the ankle pulse wave and the upper arm pulse wave used for the calculation of the pulse wave velocity PWV was normally measured, for example, first, the determination conditions indicated in the followings will be determined on each of the ankle pulse wave and upper arm pulse wave. Specifically, it is judged whether or not the highest value of the pulse wave is in the predetermined ratio range which spans over the pulse wave making the highest value of a certain pulse wave (prior to or subsequent to the pulse wave) being the center of the range (first condition), whether or not the lowest value of the pulse wave is in the predetermined ratio range which spans over the pulse wave making the lowest value of a certain pulse wave (prior to or subsequent to the pulse wave) being the center of the range (second condition), whether or not the location indicating the highest value in the pulse wave by the portion of one pulse within the predetermined interval which has been preset (third condition), and whether or not the number of zero crossing points of the differential value of the pulse wave is the predetermined number or less (fourth condition). Then, even in the case where one of these conditions is not satisfied, it is judged that the pulse wave is not normally measured, and in the case where the number of pulse waves judged to have not been normally measured is the predetermined ratio or more, it is judged that the signal used for the calculation of the average pulse wave velocity $PWV_{AV}$ is not normally measured.

Figure 4:
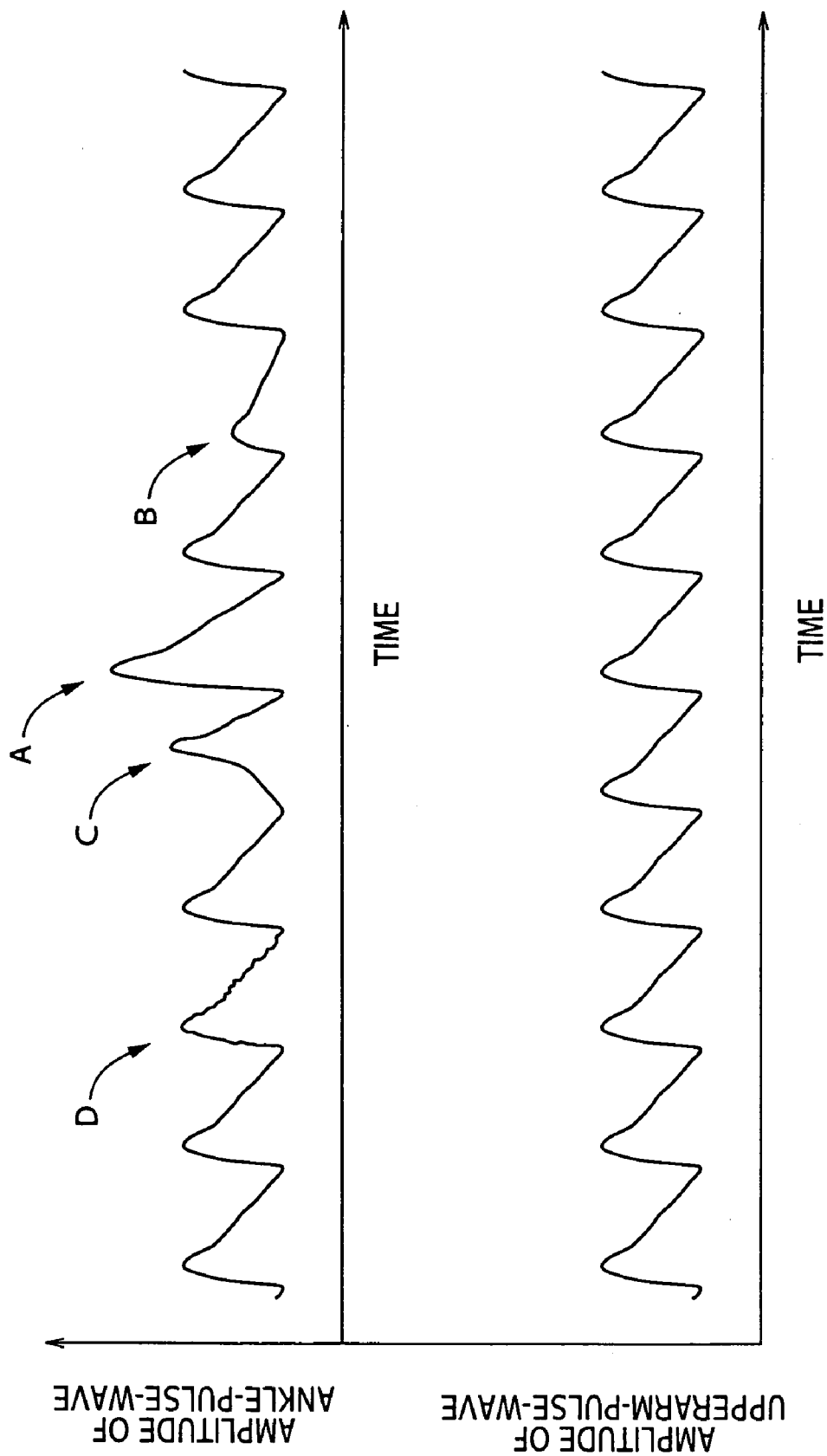
FIG. 4 is a diagram for indicating a pulse wave indicated on the display in the case where it has been judged whether or not a signal used for the determination of the average pulse wave velocity $PWV_{AV}$ is not normally measured.

Measurement results determining means 80 indicates the amplitude row as shown in the above-described FIG. 3 as a characteristic value of a plurality of pulse waves that the signal which is judged to have not been normally measured represents in the case where the means for judging the measurement results 80 has judged the ankle pulse wave signal $SM_A$ used for the determination of the ankle blood pressure value BP(A) or the upper arm pulse wave signal $SM_B$ used for the determining the upper arm blood pressure value BP(B) is not normally measured. Moreover, in the case where the means for judging the measurement results 80 has judged that the signal used for the determination of the average pulse wave velocity $PWV_{AV}$ is not normally measured, the means for judging the measurement results 80 indicates the ankle pulse wave and the upper arm pulse wave used for the determination of the pulse wave velocity PWV on the display 56. FIG. 4 is a figure showing the pulse wave indicated on the display 56 in the case where the signal used for the determination of the average pulse wave velocity $PWV_{AV}$ is judged to have not been normally measured. It should be noted that the ankle pulse waves shown in FIG. 4 is not a pulse wave actually measured but indicates the pulse waves not satisfying the respective determination conditions one by one, respectively, in order to explain the aforementioned determination conditions, the pulse wave A is a pulse wave not satisfying the first condition, the pulse wave B is a pulse wave not satisfying the second condition, the pulse wave C is a pulse wave not satisfying the third condition, and the pulse wave D is a pulse wave not satisfying the fourth condition.

Output control means 82 automatically makes the printer 58 print out the ankle blood pressure value BP(A) the upper arm blood pressure value BP(B), the ankle and upper arm blood pressure index ABI and the average pulse wave velocity $PWV_{AV}$ in the case where it has been judged by the means for judging the measurement results 80 that all of the signals used for the determination of the ankle blood pressure value BP(A), the upper arm blood pressure value BP(B) and the average pulse wave velocity $PMV_{AV}$ are normally measured, however, in the case where it has been judged that the signal used for the determination of at least any one of the ankle blood pressure value BP(A), the upper arm blood pressure value BP(B) and the average pulse wave velocity $PMV_{AV}$ are not normally measured, the output control means 82 does not make the printer 58 automatically output the ankle blood pressure value BP(A), the upper arm blood value BP(B), the ankle and upper arm blood pressure index ABI and the average pulse wave velocity $PMV_{AV}$, and only in the case where the output command signal was supplied by the output command button 62 being operated, the output control means 82 makes the printer 58 print out the ankle blood pressure value BP(A), the upper arm blood pressure value BP(B), and the ankle and upper arm blood pressure index ABI and the average pulse wave velocity $PMV_{AV}$.

Message display means 84 indicates on the display a message requesting the judgement on whether or not these values of the ankle blood pressure value BP(A), the upper arm blood pressure BP(B), the ankle and upper arm blood pressure index ABI and the average pulse wave velocity $PMV_{AV}$ are output from the printer 58 as well as indicates on the display 56 which measurement of vital-information has the possibility of abnormality in the case where it has been judged that the signal used for the determination of at least any one of the ankle blood pressure value BP(A), the upper arm blood pressure value BP(B) and the average pulse wave velocity $PMV_{AV}$ are not normally measured by the means for judging the measurement results 80. In the case where such message was indicated, on the display 56, since the amplitude row exemplified in FIG. 3 and/or the pulse wave as exemplified in FIG. 4 are indicated, whether or not the abnormality of the signal which judged as being abnormally measured by the present device 10 is caused by noises such as body movement and the like or by the disease of the patient, the physician or the other co-medical like finally can judge from the indication of the display 56, and in the case where it has been judged that the measurement is normal, the measurement results can be output from the printer 58 by operating the output indicting button 62.

Figure 5:
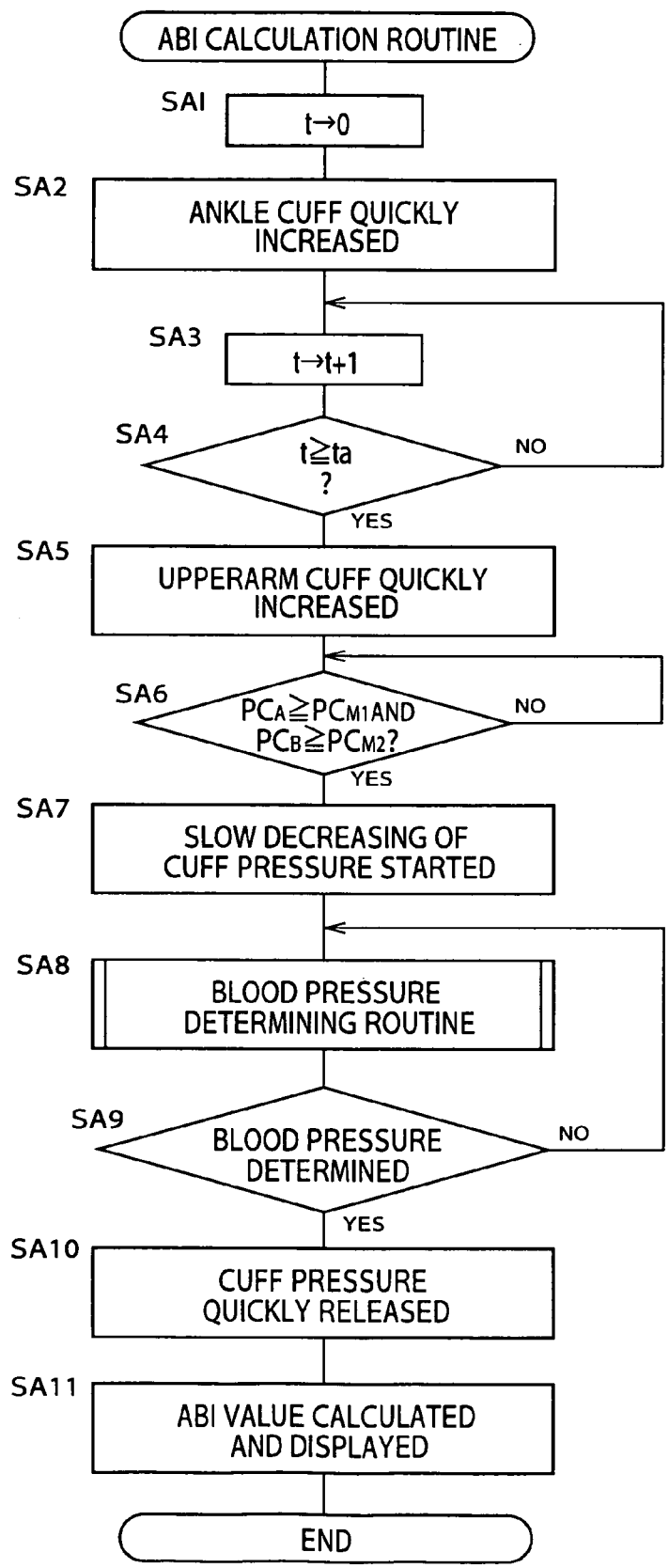
Figure 6:
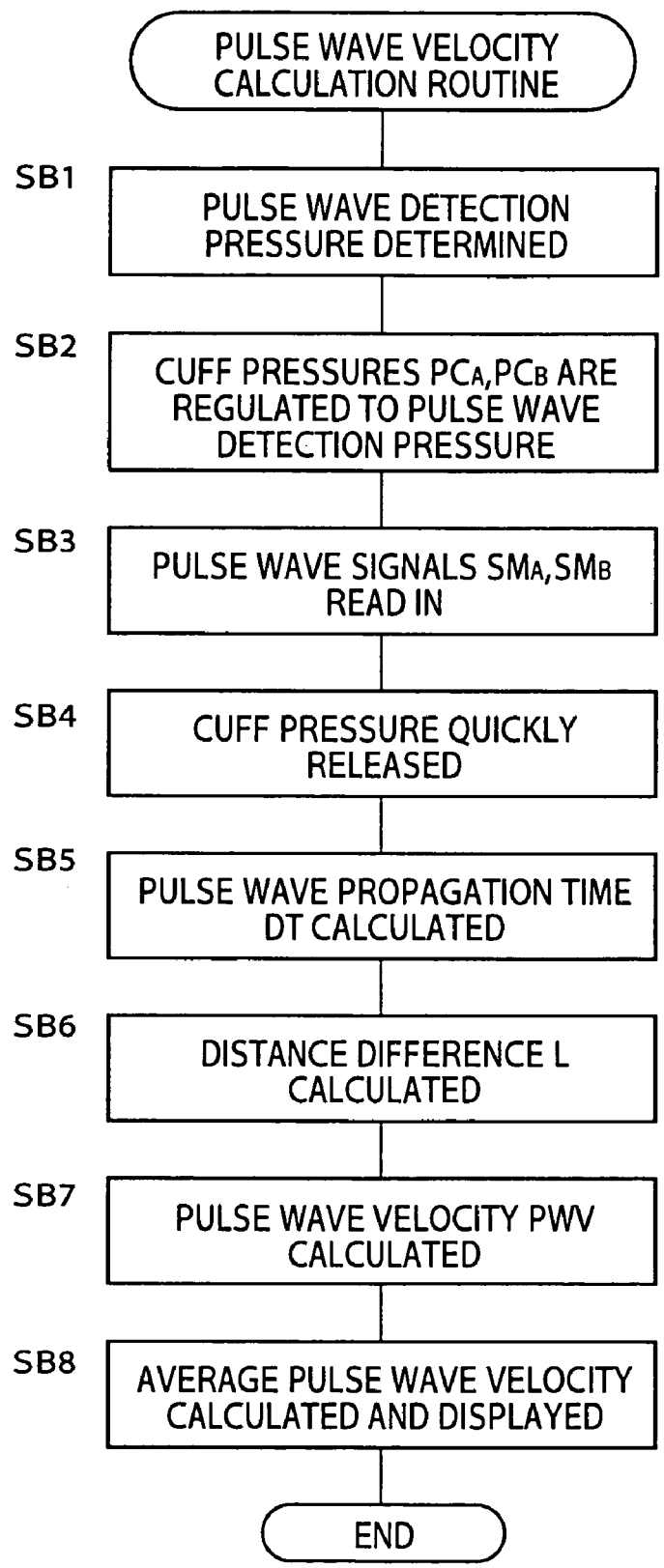
FIG. 6 is a diagram for indicating a control function of an electronic control device shown in FIG. 2 as a flowchart, and is a pulse wave velocity calculation routine which is carried out subsequent to FIG. 5.
Figure 7:
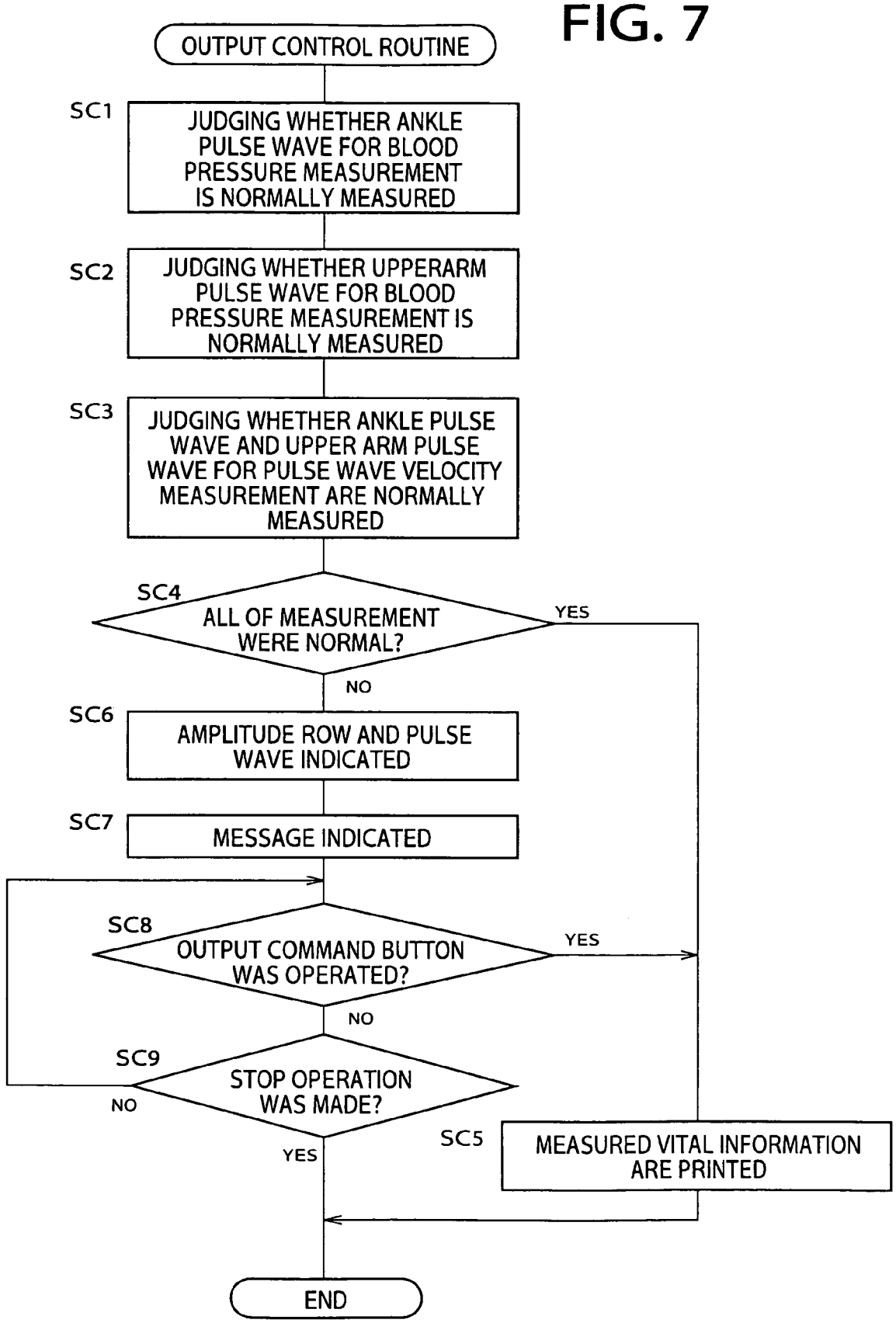
FIG. 7 is a diagram for indicating a control function of an electronic control device shown in FIG. 2 and is an output control routine which is carried out subsequent to FIG. 6.

FIG. 5 through FIG. 7 are drawings in which the control function of the electronic control device 36 shown in FIG. 2 is shown as a flowchart, FIG. 5 is the ankle and upper arm blood pressure index ABI calculation routine, FIG. 6 is the pulse wave velocity calculation routine which is to be carried out subsequent to FIG. 5, and FIG. 7 is the output control routine which is to be carried out subsequent to FIG. 6. It should be noted that the flowchart of FIG. 5 is started by the operation of the start button which is not shown under the condition in which the body height signal ST representing the body height T of the patient has been previously supplied from the input device 60.

In FIG. 5, first, in the step SA1 (hereinafter, the term "step" will be omitted), "0" is input into the contents of a timer t. In the subsequent SA2, the rapid rising up of the pressure of the ankle cuff pressure $PC_A$ is started by driving the air pump 28 and controlling the pressure regulating valve 26. Then, in the subsequent SA3, "1" is added to the contents of the timer t, and in the subsequent SA4, whether or not the timer t has exceeded over the delayed time ta previously set is determined. This delay time ta is a time previously set in order that the ankle cuff pressure $PC_A$ and the upper arm cuff pressure $PC_B$ are made reach to the respective target pressure values $PC_{M1}$, $PC_{M2}$ at approximately the same time.

In the case where the determination of the above-described SA4 was denied, the rising up of the pressure of the ankle cuff pressure $PC_A$ is continued as well as the elapsed time from the initiation of the rising up of the pressure of the ankle cuff pressure $PC_A$ is measured. On the other hand, in the case where the determination of the SA4 has been affirmed, in the subsequent SA5, the rapid rising up of the pressure of the upper arm cuff pressure $PC_B$ is initiated by driving the air pump 47 and controlling the pressure regulating valve 46.

In the subsequent SA6, it is judged whether or not the ankle cuff pressure $PC_A$ has been the value of the first target pressure value $PC_{M1}$ which had been set, for example, at 240 mmHg, or more and whether or not the upper arm cuff pressure $PC_B$ has been the value of the second target pressure value $PC_{M2}$ which had been set, for example, at 180 mmHg or more. In the case where this determination has been denied, the determination of the SA6 is repeatedly carried out. On the other hand, in the case where this determination has been affirmed, in the subsequent SA7, the ankle cuff pressure $PC_A$ and the upper arm cuff pressure $PC_B$ are gradually lowered at the rate on the order of 3–5 mmHg/sec previously set.

Subsequently, in the SA8 corresponding to the means for determining the ankle blood pressure value 72 and the means for determining the upper arm blood pressure value 74, the blood pressure value determination routine is carried out. Specifically, an amplitude row is prepared from the amplitude of the ankle pulse wave represented by the ankle pulse wave signal $SM_A$ which is in turn supplied from the pulse wave discrimination circuit 32, and further, the amplitude row is smoothed, the blood pressure value determination algorithm of the aforementioned oscillometric method is carried out based on the amplitude row after the smoothing, the ankle highest blood pressure value $BP(A)_{SYS}$, the ankle mean blood pressure value $BP(A)_{MEAN}$, and the ankle lowest blood pressure value $BP(A)_{DIA}$, are determined, and the upper arm highest blood pressure value $BP(B)_{SYS}$, the ankle mean blood pressure value $BP(B)_{MEAN}$, and the ankle lowest blood pressure value $BP(B)_{DIA}$ are determined from the amplitude of the upper arm pulse wave represented by the upper arm pulse wave signal $SM_B$ which is in turn supplied from the pulse wave discrimination circuit 50 similar to the case of the ankle blood pressure value BP(A).

In the SA9 subsequent to the SA8, it is judged whether or not the determination of the blood pressure value BP is completed. Since in the process of gradually lowering pressure the cuff pressure $PC_A$, $PC_B$, the lowest blood pressure value $BP(A)_{DIA}$ and $BP(B)_{DIA}$ is finally determined, in the SA9, it is judged whether or not these lowest blood pressure value $BP(A)_{DIA}$, and $BP(B)_{DIA}$ has been determined. In the case where the determination of this SA9 has been denied, the aforementioned SA8 and subsequent steps are repeatedly carried out. On the other hand, in the case where the determination of the SA9 has been affirmed, in the subsequent SA10, the ankle cuff pressure $PC_A$ and the upper arm cuff pressure $PC_B$ are pressurized and exhausted to the atmospheric pressure by controlling the pressure regulating valves 26, 46.

Subsequently, in the SA11 corresponding to the means for calculating the ankle and upper arm blood pressure index 76, the ankle and upper arm blood pressure index ABI is calculated by dividing the ankle highest blood pressure value $BP(A)_{SYS}$ determined in the aforementioned SA8 by the upper arm highest blood pressure value $BP(B)_{SYS}$ determined in the same aforementioned SA8, and the calculated ankle and upper arm blood pressure index ABI is indicated on the display 56. Then, after the SA11 has been carried out, the pulse wave velocity calculation routine of FIG. 6 is carried out.

Subsequently, the pulse wave velocity calculation routine of FIG. 6 will be explained. First, in the SB1, the pulse wave detection pressure in the upper arm 14 is determined by subtracting the above-described predetermined value a from the ankle lowest blood pressure value $BP(A)_{DIA}$ determined in the SA8 of FIG. 5 as well as the pulse wave detection pressure in the ankle 12 is determined by subtracting the predetermined value α set on the order of 10 mmHg from the ankle lowest blood value $BP(A)_{DIA}$ determined in the SA8 of FIG. 5. Then, in the subsequent SB2, the ankle cuff pressure $PC_A$ and the upper arm cuff pressure $PC_B$ are regulated to the pulse wave detection pressure determined in the above-described SB1, respectively, and the cuff pressure PC is maintained by driving the air pumps 28, 47 again and controlling the pressure regulating valves 26, 46.

In the subsequent SB3, the ankle pulse wave signal $SM_A$ supplied from the pulse wave discrimination circuit 32 and the upper arm pulse wave signal $SM_B$ supplied from the pulse wave discrimination circuit 50 are read by the portion of 10 pulses, respectively. Then, when these signals are read, in the subsequent SB4, the ankle cuff pressure $PC_A$ and the upper arm cuff pressure $PC_B$ is pressurized and exhausted and these values of the ankle cuff pressure $PC_A$ and the upper arm cuff pressure $PC_B$ are made atmospheric pressure by stopping the air pumps 28, 47 and controlling the pressure regulating valves 26, 46. In the flow chart shown in FIG. 5 and FIG. 6, the SA1 through the SA7, the SA10, the SB1 through the SB2, SB4 correspond to the cuff control means 70.

Subsequently, the SB5 through the SB8 corresponding to the means for calculating the pulse wave velocity 78 are carried out. First, in the SB5, the rise up points of the ankle pulse wave and the upper arm pulse wave by the portion of 10 pulses read in the aforementioned SB3 are determined, respectively, the pulse wave propagation time DT by the portion of 10 pulses is calculated from the time difference between the rise up points of the respective upper arm pulse waves and the rise up points of the ankle pulse waves corresponding to the upper arm pulse waves.

Then, in the subsequent SB6, the distance difference L is calculated by substituting the body height T of the patient which has been previously supplied into the aforementioned expression, in the subsequent SB7, the pulse wave velocity PWV by the portion of 10 pulses is calculated by substituting the respective pulse wave propagation times DTs calculated in the SB5 and the distance difference L calculated in the above-described SB6 into the aforementioned expression 2. Then, in the subsequent SB8, the average pulse wave velocity $PMV_{AV}$ is calculated by averaging the pulse wave velocity PWV by the portion of 10 pulses calculated in the above-described SB7, and the calculated average pulse wave velocity $PMV_{AV}$ is indicated on the display 56. After this SB8 has been carried out, the output control routine of FIG. 7 is carried out.

Subsequently, the output control routine of FIG. 7 is explained. First, in the SC1, in order to determine whether or not the ankle pulse wave read for determining the ankle blood pressure value BP(A), that is, the ankle pulse wave signal $SM_A$ read in the SA8 of FIG. 5 is a signal normally measured, for example, as described above, first, the amplitude difference between the amplitude before the smoothing and the amplitude after the smoothing is calculated each pulse wave and the percentage of he sum of the amplitude difference with respect to the sum of the amplitude value after the smoothing is calculated as a correction factor. Then, in the case where the correction factor is the predetermined reference value or more, it is judged that the measurement of the ankle pulse wave signal $SM_A$ was abnormal.

In the subsequent SC2, it is judged as similar to the above-described SC1 whether or not the upper arm pulse wave read in order to determine the upper arm blood pressure value BP(B), that is, the ankle pulse wave signal $SM_A$ read in the SA8 of FIG. 5 is a signal normally measured.

In the subsequent SC3, it is judged whether or not the ankle pulse wave and the upper arm pulse wave by the portion of 10 pulses read in order to calculate the average pulse wave velocity $PMV_{AV}$ satisfy the aforementioned first condition through the fourth condition, respectively, and in the case where the number of pulse waves not satisfying at least one of the first condition through the fourth condition is the predetermined ratio or more, it is judged that the signal used for the calculation of the average pulse wave velocity $PMV_{AV}$ has been not normally measured.

Then, in the subsequent SC4, it is judged whether or not it has been judged that all of the measurements were normal, that is, in the above-described SC1, whether or not it has been judged that the measurement of the ankle pulse wave for judging the ankle blood pressure value BP(A) is normal, in the above-described SC2, it is judged whether or not it has been judged that the measurement of the upper arm pulse wave for judging the upper arm blood pressure value BP(B) is normal, and in the above-described SC3, whether or not it has been judged that the measurement of the ankle pulse wave and the upper arm pulse wave for judging the average pulse wave velocity $PMV_{AV}$ is normal.

In the case where the determination of the above-described SC4 has been affirmed, in the SC5, after the ankle blood pressure value BP(A), the upper arm blood pressure value BP(B), the ankle and upper arm blood pressure index ABI and the average pulse wave velocity $PMV_{AV}$ has been output from the printer 58, the present routine is terminated.

On the other hand, in the case where the determination of the above-described SC4 has been denied, that is, in the case where it has been judged that at least any one of the measurements is abnormal, the subsequent SC6 is carried out. In the SC6, in the case where it has been judged that the measurement of the ankle pulse wave for judging the ankle blood pressure value is abnormal, the amplitude row of the ankle pulse wave is indicated on the display 56, in the aforementioned SC2, in the case where it has been judged that the measurement of the upper arm pulse wave for judging the upper arm blood pressure value is abnormal, the amplitude row of the upper arm pulse wave is indicated on the display 56, and in the aforementioned SC3, the ankle pulse wave and the upper arm pulse wave used for the determination of the average pulse wave velocity $PMV_{AV}$ are indicated on the display 56. In FIG. 7, the SC1–SC3 and the SC6 correspond to the means for judging the measurement results 80.

The subsequent SC7 corresponds to the message indicating means 84, concerning the vital-information judged as being abnormal when measured in the aforementioned SC1 through the SC3, a message that there is a possibility of abnormal measurement and a message requesting the judgement on whether or not the ankle blood pressure value BP(A), the upper arm blood pressure value BP(B), the ankle and upper arm blood pressure index ABI and the average pulse wave velocity $PMV_{AV}$ are output from the printer 58 is indicated on the display 56.

Then, in the subsequent SC8, it is judged whether or not the output command button 62 has been operated. In FIG. 7, the SC4, the SC5 and the SC8 correspond to the output control means 82. In the case where the determination of the SC8 has been affirmed, the aforementioned SC5 is carried out, the ankle blood pressure value BP(A), the upper arm blood pressure value BP(B), the ankle and upper arm blood pressure index ABI and the average pulse wave velocity $PMV_{AV}$ are output from the printer 58. On the other hand, in the case where the determination of the SC8 has been denied, in the subsequent SC9, it is further judged whether or not the stop operation has been made. In the case where this determination has been denied, the determinations of the SC8 and the SC9 are repeatedly carried out until the output command button 62 is operated or the stop operation is made. On the other hand, in the case where the determination of the SC9 has been affirmed, the present routine is terminated.

According to the above-described embodiment, the measurement results judging means 80 (SC1–SC3 and SC6) judges whether or not the measurement of vital signal (specifically, the ankle pulse wave signal $SM_A$, the upper arm pulse wave signal $SM_B$) has been normal. In the case where it has been judged that all of the measurements of the vital signal used for the measurement of such plurality of vital-information are normal, since the above-described plurality of vital-information are automatically output from the printer 58, the troublesome works of the printing operation can be omitted, and in the case where it has been judged that the measurement of the vital signals used for the determination of at least one of the vital-information is not normal, the above-described vital-information is not output from the printer 58, therefore, unnecessary vital-information can be prevented from being output from the printer 58.

Moreover, according to the above-described embodiment, in the case where it has been judged by the measurement results judging means 80 (SC1–SC3 and SC6) that the measurement of the above-described vital-information signals are not normal, the amplitude row of the ankle pulse wave used for the determination of the ankle blood pressure value BP(A), and/or the amplitude row of the upper arm pulse wave used for the determination of the upper arm blood pressure value BP(B), and/or the ankle pulse wave and the upper arm pulse wave used for the calculation of the average pulse wave velocity $PMV_{AV}$ are indicated on the display 56, therefore, the physician or the other co-medical can determine whether or not the measurement of the above-described vital signal is normal, in the case where the operator has operated the output command button 62, then, even in the case where it has been judged by the measurement results judging means 80 (SC1–SC3, and SC6) that the measurement of the above-described vital signal is not normal, the vital-information is output from the printer. Therefore, necessary vital-information can be certainly output from the printer 58.

As described above up to this point, one Example of the present invention has been described based on the drawings, however, the present invention may be also applied to the other Embodiments.

For example, in the above-described Example, in the case where it has been judged that the measurement of the ankle pulse wave used for the determination of the ankle blood pressure value BP(A) is not normal, or in the case where it has been judged that the measurement of the upper arm pulse wave used for the determination of the upper arm blood pressure value BP(B) is not normal, the amplitude row of the ankle pulse wave or the upper arm pulse wave has been indicated on the display 56, instead of the amplitude row, or in addition to the amplitude row, the ankle pulse wave used for the determination of the ankle blood pressure value BP(A) or the upper arm pulse wave used for determination of the upper arm pressure value BP(B) may be indicated as it is on the display 56.

Moreover, in the above-described Example, the pulse wave velocity PWV has been calculated based on all of the pulse waves by the portion of 10 pulses measured, however, only in the case of the pulse wave judged that it has been normally measured by the means for judging the measurement results 80, it may be made so that the pulse wave velocity PWV would be calculated.

As described above up to this point, the mode for carrying out of the present invention has been described, however, the present invention is not limited to the above-described mode for carrying out, and can be carried out in modes to which a variety of modifications and improvements have been added based on the knowledge of those skilled in the art.

What is claimed is:

1. A vital-information measure device, comprising:
    a vital signal sensor for detecting a vital signal;
    a vital-information determining means for determining a vital-information based on the vital signal detected by the vital signal sensor;
    a printer for outputting vital information determined by the vital-information determining means;
    a measurement results judging means for judging whether or not the vital signal measured by the vital signal sensor is a signal normally measured based on a predetermined judging criterion;

an output controlling means for controlling the printer such that the printer does not print out the vital-information when the measurement of said vital signal is judged as not being normal by the judging means, and the printer prints out the vital-information when the measurement of the vital signal is judged as being normal by the judging means;

a display for indicating the vital signal used for determination of said vital-information and a characteristic value of the vital signal;

a message indicating means for indicating on the display a message requesting the judgement on whether or not the vital-information is output from said printer when the measurement of said vital signal is judged as not being normal by the measurement results judging means; and an output command button for being operated by an operator in order to print out said vital-information from said printer, wherein when the output command button is operated, even if the measurement of said vital signal has been judged as not being normal by the measurement results judging, said output controlling means controls the printer so as to output said vital-information.

2. A vital-information measuring device, comprising:

a vital signal sensor for detecting a vital signal;

a vital-information determining means for determining a vital-information based on the vital signal detected by the vital signal sensor;

a printer for outputting vital-information determined by the vital-information determining means;

a measurement results judging means for judging whether or not the vital signal measured by the vital signal sensor is a signal normally measured based on a predetermined judging criterion;

an output controlling means for controlling the printer such that the printer does not print out the vital-information when the measurement of said vital signal is judged as not being normal by the judging means, and the printer prints out the vital-information when the measurement of the vital signal is judged as being normal by the judging means, wherein the vital-information determining means determines a plurality of species of vital-information, the measurement results judging means judges the each vital-information of said plurality of species whether or not a vital signal used for judgement of the vital-information is a signal normally measured, the output controlling means controls the printer so as to automatically output the plurality of species of vital-information determined by the vital-information determining means when the measurement of the vital signals used for determination of the plurality of species of vital-information are judged as being normal by the measurement results judging means, and the output controlling means does not control the printer to output the plurality of species of vital-information determined by vital-information determining means when measurement of the vital signal used for determination of at least one of said vital-information is judged as not being normal;

a display for indicating a vital signal used for determination of said plurality of species of vital-information or a characteristic value of the vital signal;

a message indicating means for indicating a message on the display requesting judgement on whether or not said plurality of species of vital-information is output from said printer when measurement of the vital signal used for determination of at least one of said plurality of species of vital-information is judged as not being normal by the measurement results judging means; and an output command button operated by an operator in order to print out said plurality of species of vital-information from said printer, wherein said output controlling means controls the printer so as to automatically output the plurality of species of vital-information when the output command button is operated even if the measurement of said vital signal used for determination of at least one of said plurality of species of vital-information by the measurement results judging means is judged as not being normal.

* * * * *